United States Patent
Prasetiyo et al.

(10) Patent No.: US 12,247,007 B2
(45) Date of Patent: Mar. 11, 2025

(54) REFLUX ARRANGEMENT FOR DISTILLATION COLUMNS

(71) Applicant: SAUDI ARABIAN OIL COMPANY, Dhahran (SA)

(72) Inventors: Soelistiono Koesoemo Prasetiyo, Abqaiq (SA); Yazeed Menwer Almimouny, Khobar (SA); Moath Khalid Almansour, Almatar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 311 days.

(21) Appl. No.: 17/823,428

(22) Filed: Aug. 30, 2022

(65) Prior Publication Data
US 2024/0067590 A1    Feb. 29, 2024

(51) Int. Cl.
*C07C 7/04* (2006.01)
*B01D 3/42* (2006.01)
(Continued)

(52) U.S. Cl.
CPC .............. *C07C 7/04* (2013.01); *B01D 3/4233* (2013.01); *C07C 7/005* (2013.01); *C10L 3/10* (2013.01);
(Continued)

(58) Field of Classification Search
CPC ........................... F25J 2200/72; F25J 2200/70
See application file for complete search history.

(56) References Cited

U.S. PATENT DOCUMENTS

| | | | | | |
|---|---|---|---|---|---|
| 5,588,308 | A | * | 12/1996 | Daugherty | F25J 3/0242 62/622 |
| 8,209,996 | B2 | * | 7/2012 | Mak | F25J 3/0238 62/620 |

(Continued)

FOREIGN PATENT DOCUMENTS

| WO | 2004/057253 A2 | 7/2004 |
|---|---|---|
| WO | 2009/023252 A1 | 2/2009 |
| WO | 20160012250 A1 | 1/2016 |

OTHER PUBLICATIONS

ISR-WO for PCT/US2023/031424 dated Nov. 28, 2023 and that claims priority to this application.
(Continued)

*Primary Examiner* — Filip Zec
(74) *Attorney, Agent, or Firm* — Vorys, Sater, Seymour and Pease LLP

(57) ABSTRACT

The present disclosure relates to systems and/or methods for enabling a reflux process in one or more distillation columns. For example, various embodiments described herein can relate to a method that can utilize the column's feed stream to provide an internal reflux mechanism in the top portion of the distillation column. For instance, the method can include capturing overhead vapor from a distillation column. Additionally, the method can include comingling the overhead vapor with a feed stream. Further, the method can include partially condensing the feed stream to form a liquid hydrocarbon feed stream that is supplied to a top portion of the distillation column. In one or more embodiments, the comingling can incorporate reflux functionality into the liquid hydrocarbon feed stream to promote a rectification process in the top portion of the distillation column.

15 Claims, 2 Drawing Sheets

(51) Int. Cl.
*C07C 7/00* (2006.01)
*C10L 3/10* (2006.01)
*F25J 3/02* (2006.01)

(52) U.S. Cl.
CPC ....... F25J 3/0238 (2013.01); *C10L 2290/543* (2013.01); *F25J 2200/06* (2013.01); *F25J 2200/72* (2013.01); *F25J 2210/04* (2013.01); *F25J 2215/62* (2013.01); *F25J 2245/02* (2013.01); *F25J 2270/90* (2013.01)

(56) References Cited

U.S. PATENT DOCUMENTS

| | | | | |
|---|---|---|---|---|
| 8,663,461 | B2* | 3/2014 | Lee | C07C 7/08 |
| | | | | 203/55 |
| 9,291,387 | B2* | 3/2016 | Malsam | F25J 3/0209 |
| 9,803,917 | B2* | 10/2017 | Burmberger | F25J 1/005 |
| 10,370,598 | B2* | 8/2019 | Van Leeuwen | F25J 1/0231 |
| 10,436,505 | B2* | 10/2019 | Jiang | F25J 3/0271 |
| 10,443,930 | B2* | 10/2019 | Jiang | F25J 3/0233 |
| 10,981,103 | B2* | 4/2021 | Parsnick | F25J 3/04812 |
| 2008/0016910 | A1* | 1/2008 | Brostow | F25J 1/0262 |
| | | | | 62/612 |
| 2009/0188279 | A1* | 7/2009 | Bras | F25J 3/0247 |
| | | | | 62/620 |
| 2013/0213087 | A1* | 8/2013 | Currence | F25J 3/0233 |
| | | | | 62/621 |
| 2014/0260421 | A1* | 9/2014 | Lee | F25J 3/0238 |
| | | | | 62/636 |
| 2016/0102908 | A1* | 4/2016 | Johnston | F25J 1/0216 |
| | | | | 62/613 |
| 2016/0258675 | A1* | 9/2016 | Kumar | F25J 3/0257 |
| 2019/0128600 | A1* | 5/2019 | Yamamori | F25J 3/0233 |

OTHER PUBLICATIONS

Willam L. Luyben, "NGL Demethanizer Control", Industrial & Engineering CHemistry Research, vol. 52 No. 33, Aug. 9, 2013, pp. 11626-11638.

Paradowski, Henri, Andre Le-Gall and Benoît Laflotte. "Compare the Different Options for NGL Recovery From Natural Gas." (2005).

Hussain, Dr. Ya; Equilibrium Separation Column; pp. 108-123.

Khabibullin, Eldar et al., TKP4170 Process Design. Project (2010).

Erbar, John Harold; Multicomponent Distillation without External Reflux; (1958).

Linde Engineering; Natural Gas Processing Plants; retrieved from https://www.linde-engineering.com/en/process-plants/lng-and-natural-gas-processing-plants/index.html.

* cited by examiner

REFLUX ARRANGEMENT FOR DISTILLATION COLUMNS

FIELD OF THE DISCLOSURE

The present disclosure relates generally to reflux arrangements for distillation columns and, more particularly, to comingling overhead vapor from a distillation column with the column's feed stream such that the feed stream can introduce a reflux process into the distillation column to promote a rectification process.

BACKGROUND OF THE DISCLOSURE

Distillation columns are typically employed in natural gas liquid ("NGL") processing plants, where NGLs are fractioned into their base components to capture high purity products. Natural gas liquids (NGL) are components of natural gas (methane) that are separated from the gas state in the form of liquids. Natural gas liquids are valuable as separate products, and it is profitable to remove NGL from the natural gas. The liquids are first extracted from the natural gas and later fractionated into different components. Generally NGL refers to ethane, propane, butane, isobutane, pentane, and molecules heavier than pentane (C5+). The NGLs can be fractioned by heating a NGL feed stream through one or more distillation columns that leverage the differing boiling points of the various hydrocarbon components to execute the fractionation. As the feed stream is heated in the distillation column, the hydrocarbon component having the lowest boiling point is first to boil off and be captured as overhead vapor, which can be condensed and/or otherwise routed to product storage. In some instances, the overhead vapor can be condensed into a reflux stream, which can be re-introduced into the top of the distillation column.

The hydrocarbon components having a higher boiling point (e.g., the heavier components of the NGLs) can be collected at the bottom of the distillation column and routed to one or more additional distillation columns for further processing. Example of such additional distillation columns can include deethanizer columns, depropanizer columns, and/or debutanizer columns. Further, various types of distillation columns can be connected in series to capture multiple NGL products from the NGL feed stream.

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

According to an embodiment consistent with the present disclosure, a method is provided. The method can comprise capturing overhead vapor from a distillation column. The method can also comprise comingling the overhead vapor with a feed stream. Further, the method can comprise partially condensing the feed stream to form a liquid hydrocarbon feed stream that is supplied to a top portion of the distillation column. In various embodiments, the comingling can incorporate reflux functionality into the liquid hydrocarbon feed stream to promote a rectification process in the top portion of the distillation column.

In another embodiment, a system is provided. The system can comprise a piping circuit is coupled to a top section of a distillation column. The piping circuit can be configured to capture overhead vapor from the distillation column. The system can also comprise a control valve positioned along the piping circuit. The control valve can be configured to control introduction of the overhead vapor to a non-cooled feed stream. Further, the system can comprise a cooling unit in fluid communication with the non-cooled feed stream. The cooling unit can be configured to cool the non-cooled feed stream and form a liquid hydrocarbon feed stream. The piping circuit can be further configured to supply the liquid hydrocarbon feed stream to the distillation column.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Figure 1:
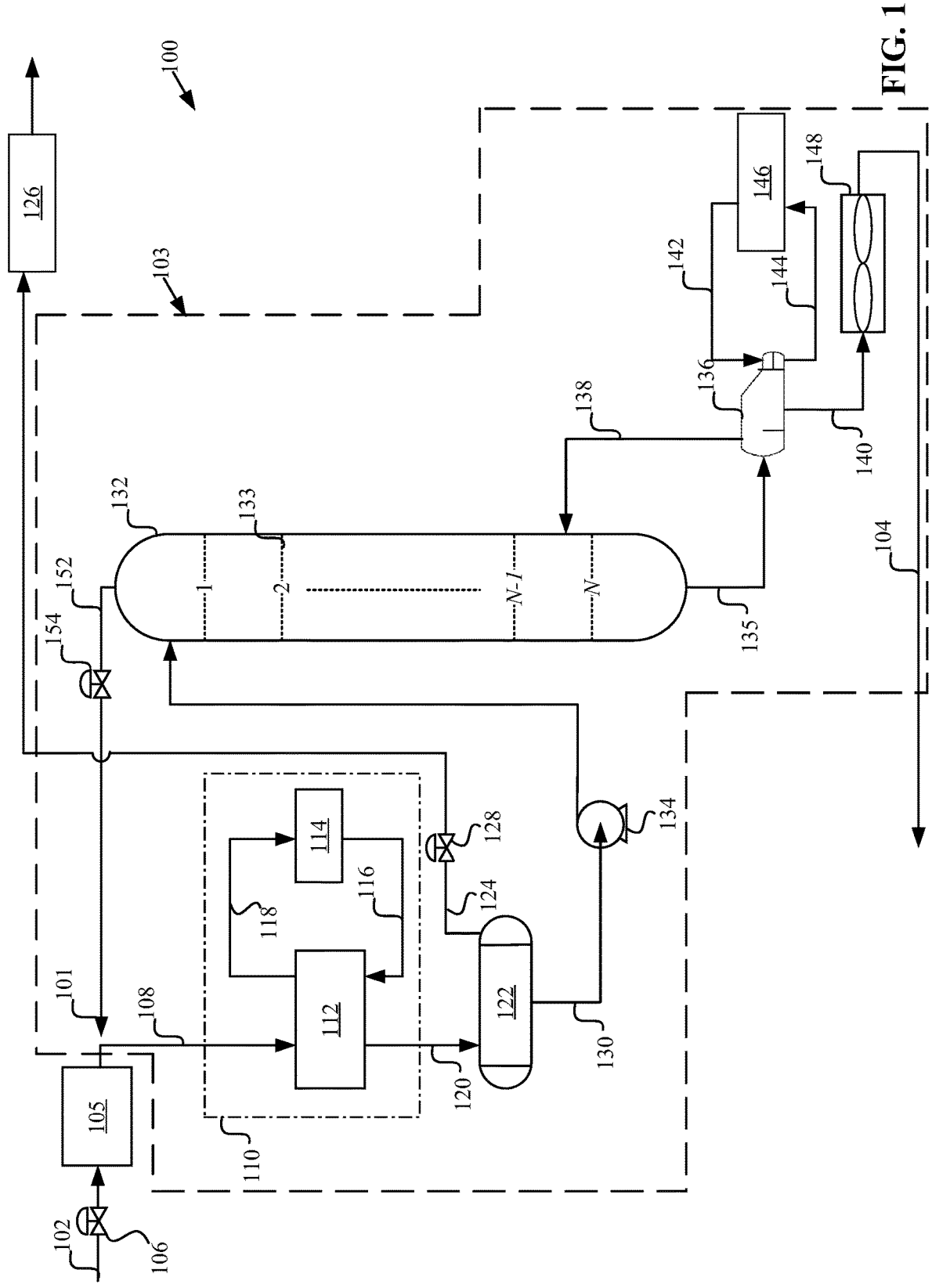
FIG. 1 is a diagram of a non-limiting example NGL processing system that can utilize a pseudo reflux feed stream to supply a distillation column and separate one or more NGL products from an offgas stream in accordance with one or more embodiments described herein.

Embodiments of the present disclosure will now be described in detail with reference to the accompanying Figures. Like elements in the various figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

As used herein, the term "coupled" or "coupled to" or "connected" or "connected to" or "attached" or "attached to" may indicate establishing either a direct or indirect connection, and is not limited to either unless expressly referenced as such. Wherever possible, like or identical reference numerals are used in the figures to identify common or the same elements. The figures are not necessarily to scale and certain features and certain views of the figures may be shown exaggerated in scale for purposes of clarification.

Typically, NGL processing systems comprise multiple cooling stages. For example, the NGL feed stream is processed by a first chilling system to condense the feed stream prior to introduction into the distillation column. The captured overhead vapor from the distillation column is then processed by a second chilling system to condense the overhead vapor into a reflux stream that can be re-introduced to the distillation column as another stream, distinct from the feed stream. As a result of the multiple cooling stages, typical NGL processing systems have respective equipment necessities for each of the feed stream and the reflux stream. Further, each cooling stage of the conventional systems require a respective condenser, reservoir drum, pump, and/or piping circuits. As the equipment requirements of a NGL processing system increase; so too does the cost of the system, the maintenance requirements of the system, and/or the system's likelihood of failure.

Embodiments in accordance with the present disclosure generally relate to reflux arrangements for distillation columns that minimize the equipment count of a NGL processing system by utilizing a cooling stage that incorporates captured overhead vapor directly into the feed stream prior to introduction into the distillation column, rendering a pseudo reflux stream. One or more embodiments described herein include a piping circuit that routes overhead vapor from a distillation column back to a cooling stage that directly chills the NGL feed stream. Thereby, the captured overhead vapor is comingled with the NGL feed stream. In various embodiments, the feed stream is directed to the top of the distillation column, such that the captured overhead vapor component in the feed stream can provide internal reflux process for top trays positioned in the distillation column.

FIG. 1 illustrates a diagram of a non-limiting example NGL processing system 100 that can employ a pseudo reflux feed stream in accordance with one or more embodiments described herein. As shown in FIG. 1, the NGL processing system 100 can include one or more piping circuits 101 to carry and/or route fluids between various features of the system 100. For example, FIG. 1 depicts the one or more piping circuits 101 via solid arrows, where the direction of the arrows can indicated the direction of flow within the piping circuit 101. In various embodiments, the one or more fluid streams (e.g., gas streams and/or liquid streams) can be housed, carried, and/or routed within the piping circuit 101. For instance, respective sections of the piping circuit 101 can route respective fluid streams between components of the system 100 in accordance with various embodiments described herein.

In various embodiments, the NGL processing system 100 can separate one or more desired NGL products from an NGL offgas stream 102. In one or more embodiments, the NGL offgas stream 102 can be the product from one or more separators at an oil terminal and/or the overhead fraction from a crude distillation column in a refinery. For example, raw natural gas can be treated to remove acid gasses (e.g., hydrogen sulfide and/or carbon dioxide), mercury, nitrogen, and/or methane to achieve the NGL offgas stream 102. For each respective NGL product, the NGL processing system 100 can include a processing module 103. While FIG. 1 depicts an example embodiment of the NGL processing system 100 comprising a single processing module 103, the architecture of the NGL processing system 100 is not so limited. For example, embodiments in which the NGL processing system 100 includes multiple processing modules 103 are also envisaged. For instance, the NGL processing system 100 can include, but is not limited to: an ethane separation processing module 103, a propane separation processing module, and/or a butane separation processing module 103. In one or more embodiments, the equipment features of the one or more processing modules 103 can be the same, or nearly the same, but configured to operate at different temperatures and/or pressures per processing module 103 to facilitate separation of the respective NGL product. Further, in some embodiments multiple processing modules 103 can be connected in series such that the residual NGL stream 104 of one processing module 103 can be fed to another processing module 103 to facilitate the extraction of another desired NGL product.

In various embodiments, the NGL offgas stream 102 can be a product of one or more stages of natural gas processing, including, but not limited to: gas-oil separation, condensate separation, contaminant removal, and/or methane separation. For example, the NGL offgas stream 102 can comprise various NGL components, such as: ethane, propane, i-butane, b-butane, i-pentane, n-pentane, n-hexane, and/or C7+ hydrocarbons. The NGL processing system 100 can control the supply of the NGL offgas stream 102 to a dehydration system 105 via a control valve 106. Example types of valves that can be employed herein include, but are not limited to: globe valves, butterfly valves, needle valves, a combination thereof, and/or the like. In various embodiments, the control valve 106 can regulate the pressure of the NGL offgas stream 102 such that the pressure of the NGL offgas stream 102 ranges from, for example, less than or equal to 31 barg.

In one or more embodiments, the water content of the NGL offgas stream 102 can be reduced in dehydration system 105 to mitigate the formation of hydrates (e.g., decrease the amount and/or size of hydrate particles) that may otherwise accumulate and/or plug the equipment of the NGL processing system 100. The dehydration system 105 can employ a variety of suitable methods to perform the water removal, such as using an ethylene glycol (glycol injection) system as an absorption mechanism to remove water and/or other solids from the NGL offgas stream 102. Alternatively, the dehydration system 105 can utilize a dry-bed dehydration tower (e.g., containing desiccants, such as silica gel and/or activated alumina) to perform the water extraction.

For example, the dehydration system 105 can be a triethylene glycol ("TEG") dehydration system, where the NGL offgas stream 102 can contact lean TEG in one or more columns using structured packing. For instance, the dehydration system 105 can be a TEG dehydration system configured based on: the lean TEG water content; the temperature of the NGL offgas stream 102 at the inlet of the TEG absorber (not shown) of the TEG dehydration system; the number of stages of the TEG absorber; and/or the packing efficiency of the TEG absorber (e.g., a function of packing type, bed height, and/or the quality of liquid and gas distributors). In one or more embodiments: the TEG water content can range from, for example, greater than or equal to 0.1 weight percent (wt. %) and less than or equal to 0.2 wt. %; the temperature of the NGL offgas stream 102 can range from, for example, greater than or equal to 24° C. and less than or equal to 34° C.; and/or the number of stages of the TEG absorber can range from, for example, greater than or equal to 3 stages and less than or equal to 4 stages. Thereby, the one or more dehydration systems 105 can dehydrate the NGL offgas stream 102 into a dry feed stream 108. For instance, the dry feed stream 108 can have a water content that is less than 0.02 wt. %.

In various embodiments, the dry feed stream 108 can be a non-cooled stream. For instance, a temperature of the dry feed stream 108 can range from, for example, greater than or equal to 50° C. The NGL processing system 100 can further route the dry feed stream 108 to a cooling unit 110, which can cool the dry feed stream 108. For example, one or more piping circuits 101 can be coupled to the dehydration system 100 and one or more chillers 112 and/or condensers of the cooling unit 110. In one or more embodiments, the cooling unit 110 can utilize one or more chillers/condensers 112 coupled to one or more refrigerant systems 114 to cool the dry feed stream 108. For example, the cooling unit 110 can utilize one or more refrigerant loops, where a cool refrigerant stream 116 can be supplied to the one or more chillers 112 from the refrigerant system 114. The cool refrigerant stream 116 can cycle through the one or more chillers 112 adjacent to the dry feed stream 108 to facilitate a heat exchange. Thereby, the cool refrigerant stream 116 can be heated to form a warm refrigerant stream 118, which can be returned to the refrigerant system 114 to be re-cooled. In some embodiments, the gas used as the refrigerant can be a propane refrigerant. As a result of the cooling, a cold feed stream 120 can be supplied from the one or more chillers 112 and routed to one or more feed drums 122. For example, one or more piping circuits 101 can be coupled between the one or more chillers 112 and the one or more feed drums 122. In some embodiments, the cold stream 120 can be partially condensed by the cooling unit 110.

In one or more embodiments, the cooling unit 110 can cool the dry feed stream 108 below the hydrocarbon dew point such that the cold feed stream 120 is a mixture of gas and liquid components. In various embodiments, the cooling unit 110 can cool the cold feed stream 120 to an operating temperature depending on, for example, the operating pressure of one or more distillation columns described herein (e.g., deethanizers, depropanizers, and/or debutanizers). For instance, where the processing module 103 is configured to extract ethane from the NGL offgas stream 102, the cooling unit 110 can reduce the temperature of the dry feed stream 108 such that the temperature of the cold feed stream 120 is, for example, less than or equal to 35° C. In another instance, where the processing module 103 is configured to extract propane from the NGL offgas stream 102, the cooling unit 110 can reduce the temperature of the dry feed stream 108 such that the temperature of the cold feed stream 120 is, for example, less than or equal to 57° C. In a further instance, where the processing module 103 is configured to separate butane from the NGL offgas stream 102, the cooling unit 110 can reduce the temperature of the dry feed stream 108 such that the temperature of the cold feed stream 120 is, for example, less than or equal to 57° C. (e.g., at a low operating pressure).

The non-condensed vapor component of the cold feed stream 120 can be exported from the feed drum 122 as a product stream 124 to one or more downstream gas plants by ether gravity or using an offgas compressor 126. For instance, where the processing module 103 is configured to perform an ethane separation process, the product stream 124 can be ethane vapor. As shown in FIG. 1, the product stream 124 can be regulated via a second control valve 128. The condensed liquid component of the cold feed stream 120 can be exported from the feed drum 122 as a liquid hydrocarbon feed stream 130 to a distillation column 132 via one or more feed pumps 134. For example, one or more piping circuits 101 can be coupled between the one or more feed drums 122 and the one or more feed pumps 134. Additionally, the one or more piping circuits 101 can be further coupled between the one or more feed pumps 134 and the distillation column 132. In various embodiments, the liquid hydrocarbon feed stream 130 can be supplied to a top of the distillation column 132, in some cases at the top third of the column 132, in other cases the top forth of the column 132, and in still other cases above the first tray of the column 132.

In various embodiments, the distillation column 132 can be utilized to separate an additional portion of the desired NGL product from the liquid hydrocarbon feed stream 130. For example, the distillation column 132 can be configured to perform a separation process that is based on the relative volatility of the components of the liquid hydrocarbon feed stream 130. In some embodiments, the distillation column 132 can be configured to perform one or more separation operations, including, but not limited to: absorption, rectification, striping, re-boiled stripping, re-boiled absorption, extractive distillation, and/or zeotropic distillation. For instance, the distillation column 132 can comprise a plurality of stages that facilitate one or more equilibrium or non-equilibrium separation processes. Additionally, the plurality of stages can be defined by one or more trays 133 (e.g., represented by dotted lines in FIG. 1) comprised within the distillation column 132. In one or more embodiments, the distillation column 132 can comprise N number of trays 133, where N is an integer less than or equal to 60.

In one or more embodiments, the distillation column 132 can be a deethanizer, configured to have: a top temperature that is, for example, less than or equal to 35° C.; a top pressure being, for example, greater less than or equal to 31 barg; a bottom temperature that is, for example, greater than or equal to 115° C.; and/or a bottom pressure that is, for example, less than or equal to 32 barg. In one or more embodiments, the distillation column 132 can be a depropanizer, configured to have: a top temperature that is, for example, less than or equal to 57° C.; a top pressure that is, for example, less than or equal to 22 barg; a bottom temperature that is, for example, greater than or equal to 138° C.; and/or a bottom pressure that is, for example, less than or equal to 23 barg. In one or more embodiments, the distillation column 132 can be a debutanizer, configured to have: a top temperature that is, for example, less than or equal to 57° C.; a top pressure that is, for example, less than or equal to 7 barg; a bottom temperature that is, for example, greater than or equal to 121° C.; and/or a bottom pressure that is, for example, less than or equal to 8 barg.

In one or more embodiments, heat can be supplied to the distillation column 132 via a re-boiler 136. For example, the liquid hydrocarbon feed stream 130 can travel down the distillation column 132 and exit as an export stream 135 that is supplied to the re-boiler 136, where the fluid is partially vaporized. For instance, the re-boiler 136 can heat the export stream 135, thereby creating a boil-up vapor stream 138 that is returned to the distillation column 132 (e.g., via the one or more piping circuits 101) and a residual liquid that is drawn from the re-boiler 136 as a bottom product stream 140 (e.g., via the one or more piping circuits 101). As the liquid hydrocarbon feed stream 130 travels down the distillation column 132, it can contact the vapor of the boil-up vapor 138 at various stages. Further, the re-boiler 136 can be a heat exchanger that utilizes a steam loop to heat the export stream 135 in which a hot steam stream 142 is supplied to the re-boiler 136 from a steam system 146 and a condensate stream 144 is returned to the steam system 146 for re-heating. In some embodiments, the given processing module 103 can utilize a direct-fire heater to perform the re-boiling. Additionally, one or more re-boiler circulation pumps (not shown) can be utilized to feed the re-boiler 136 and/or the direct-fire heater. In one or more embodiments, the bottom product stream 140 can be further supplied to one or more coolers 148 to render the residual NGL stream 104.

In various embodiments, the overhead vapor from the distillation column 132 can be captured as a vapor stream 152 that is controlled by a third control valve 154 and routed back to the dry feed stream 108. For example, the one or more piping circuits 101 can be coupled to a top section of the distillation column 132 and/or can introduce the vapor stream 152 back into the dry feed stream 108. In various embodiments, the vapor stream 152 can be supplied to the dry feed stream 108 at a pressure that is, for example, less than or equal to 31 barg. For example, the vapor stream 152 can be comingled with the dry feed stream 108 prior to the cooling unit 110. Thereby, reflux functionality stemming from the vapor stream 152 can be combined with the distillation column 132 feed network. As such, the cold feed stream 120, and thereby the liquid hydrocarbon feed stream 130 can serve as pseudo reflux streams. For example, re-introduction of the vapor stream 152 into the dry feed stream 108 can result in the liquid hydrocarbon feed stream 130 providing an internal reflux process for the top trays 133 of the distillation column 132. For instance, by comingling the vapor stream 152 with the dry feed stream 108, the cooling unit 110 will also partially condense the captured overhead vapor from the distillation column 132; which in turn can enable a reflux process incorporated into the cold feed stream 120 and the liquid hydrocarbon feed stream 130. The incorporation of the reflux process into the liquid hydrocarbon feed stream 130 can provide a down-flowing liquid throughout a rectification stage at the top section of the distillation column 132 to make contact with upward flowing vapor (e.g., supplied from boil-up vapor stream 138) in the distillation column 132; thereby achieving a stage-by-stage equilibrium heat and mass transfer, and a purification of the top product.

Advantageously, the processing module 103 eliminates the need for a separate cooling stage to condense just the captured overhead vapor and render the reflux process; rather cooling unit 110 can simultaneously cool the dry feed stream 108 and the overhead vapor (e.g., supplied by the vapor stream 152) to separate out the desired NGL product and render a reflux process that is incorporated into the liquid hydrocarbon feed stream 130. Further, the processing module 103 can minimize capital expenditures and/or operational expenditures by reducing the equipment requirements to implement the given NGL product separation.

Figure 2:
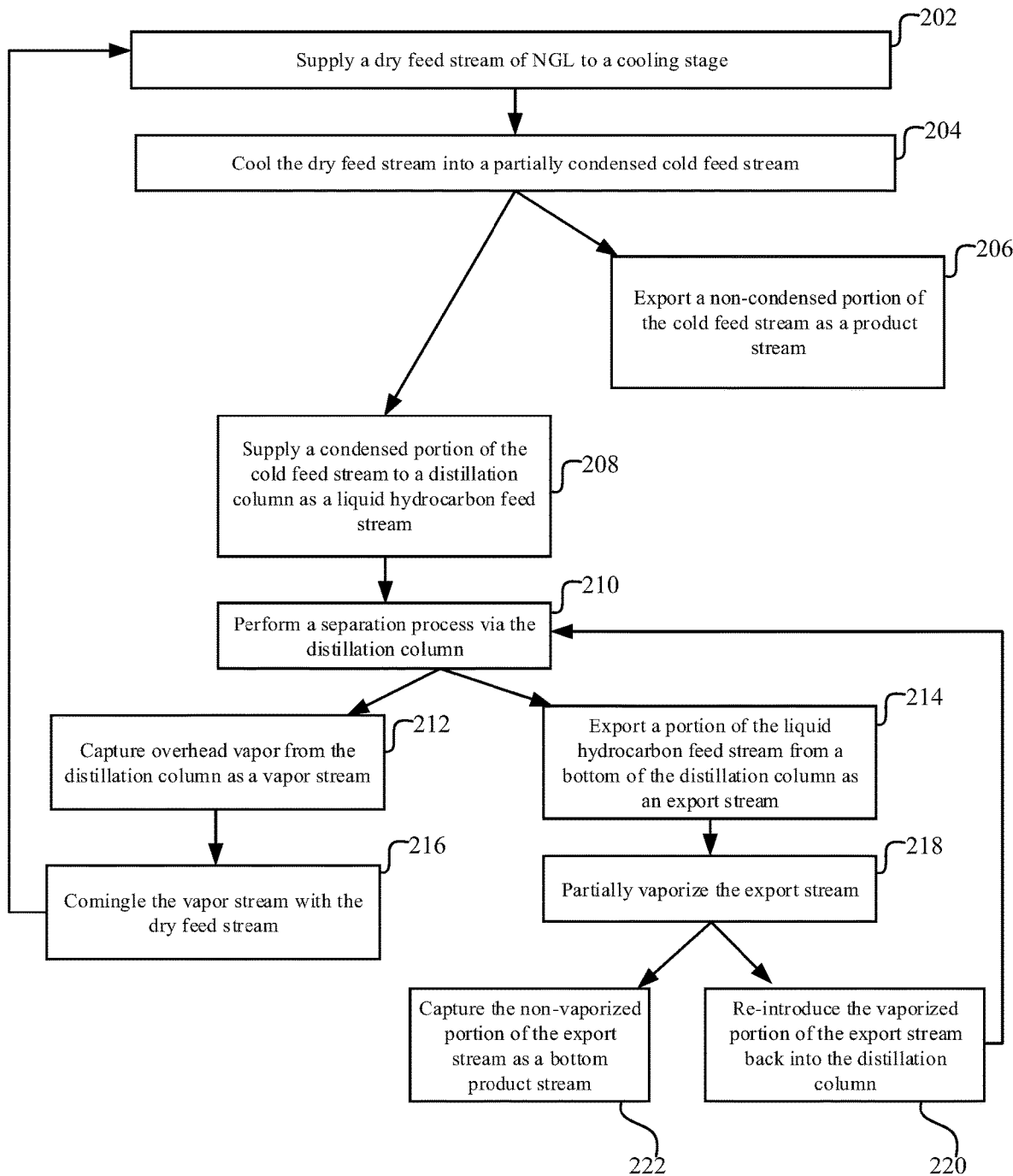
FIG. 2 is a flow diagram of a non-limiting example method that can utilize a pseudo reflux feed stream to supply a distillation column and separate one or more NGL products from an offgas stream in accordance with one or more embodiments described herein.

FIG. 2 illustrates a non-limiting example method 200 that can be implemented by one or more NGL processing systems 100 (e.g., via one or more processing modules 103) in accordance with one or more embodiments described herein. In accordance with one or more embodiments described herein, the method 200 can facilitate separation of one or more desired NGL products from a NGL offgas stream 102.

At 202, the method 200 can comprise suppling a dry feed stream 108 to a cooling unit 110. In accordance with one or more embodiments described herein, the dry feed stream 108 can be a pre-processed stream of NGLs. For example, the dry feed stream 108 can comprise a gaseous dehydrated stream of NGL components such as, but not limited to: ethane, propane, butane, pentane and/or C5+ hydrocarbons. As exemplified in FIG. 1, the dry feed stream 108 can be supplied to the cooling stage 110 via one or more pipe circuits.

At 204, the method 200 can comprise cooling the dry feed stream 108 into a partially condensed cold feed stream 120. In accordance with one or more embodiments described herein, the cooling unit 110 can comprise one or more chillers 112 and/or condensers that can reduce the temperature of the dry feed stream 108 below a hydrocarbon dew point. For example, the cooling unit 110 can utilizing one or more propane refrigeration loops (e.g., comprising a cool refrigerant stream 116 cycled to the one or more chillers 112 and/or a warm refrigerant stream 118 cycled to a refrigeration system 114). For instance, the method 200 can be employed to separate ethane from the dry feed stream 108, where the cooling at 204 can cool the temperature of the dry feed stream 108 to a temperature that is, for example, less than or equal to 35° C.

In one or more embodiments, the partially condensed cold feed stream 204 can be stored in a feed drum 122 and the method can progress to 206 and 208. At 206, the method 200 can comprise exporting a non-condensed portion of the cold feed stream 120 as a product stream 124. In accordance with one or more embodiments described herein, the non-condensed portion can comprise vapor of the desired NGL product. At 208, the method 200 can comprise supplying the condensed portion of the cold feed stream 120 to a distillation column 132 as a liquid hydrocarbon feed stream 130. In accordance with one or more embodiments described herein, a residual portion of the desired NGL product can remain trapped within the liquid hydrocarbon stream 130. Thus, the method 200 can further process the liquid hydrocarbon stream 130 to separate additional portions of the desired NGL product.

At 210, the method 200 can comprise performing a separation process via the distillation column 132. In accordance with one or more embodiments, the distillation column 132 can be, but is not limited to: a deethanizer, a depropanizer, and/or a debutanizer. Further, the distillation column 132 can comprise a plurality of trays 133 to facilitate a stage-wise separation process. For instance, the separation process can be fractional distillation process based on the volatility of the hydrocarbon components comprised within the liquid hydrocarbon stream 130. In one or more embodiments, the liquid hydrocarbon stream 130 can flow down the distillation column 132; thereby traversing through multiple zones of contact with one or more heated vapors rising up the distillation column 132. As such, the separation process can result in separating the liquid hydrocarbon feed stream 130 into a gaseous phase and a liquid phase.

Further, the method 200 can proceed (e.g., simultaneously and/or concurrently) to 212 and/or 214. At 212 the method 200 can comprise capturing the overhead vapor from the distillation column as a vapor stream 152. For example, the gaseous phase rendered by the separation process can escape from a top of the distillation column 132 as the overhead vapor. At 216, the method 200 can comprise comingling the vapor stream 152 with the dry feed stream 108. For example, FIG. 1 exemplifies routing the vapor stream 152 back to the dry feed stream 108 to re-introduce the overhead vapor from the distillation column 132 into the column's feed network. Additionally, as shown in FIG. 2, the method 200 can proceed back to 202 and supply the dry feed stream 108 (now comingled with the vapor stream 152) to the cooling unit 110.

As a result of the comingling at 216, the overhead vapor from the distillation column 132 is cooled again at the cooling unit 110, thereby incorporating reflux functionality into the cold feed stream 120. For example, following the comingling at 216, the liquid hydrocarbon feed stream 130 supplied in the subsequent iterations of feature 208 can provide an internal reflux mechanism for the top trays 133 of the distillation column 132, where a rectification process can be performed as part of the distillation.

At 214, the method 200 can comprise exporting a portion of the liquid hydrocarbon feed stream 130 from a bottom of the distillation column 132 as an export stream 135. For example, hydrocarbon components having a boiling point lower than the desired NGL product can flow down the distillation column 132 as a liquid and be exported as the export stream 135. At 218, the method 200 can comprise partially vaporizing the export stream 135. In accordance with one or more embodiments, the export stream 135 can be supplied to one or more re-boilers 136 and/or dire-fire heaters to perform the partial vaporization at 216. Further, the method 200 can proceed (e.g., simultaneously and/or concurrently) to 220 and/or 222.

At 220, the method 200 can comprise re-introducing the vaporized portion of the export stream 135 back into the distillation column 132. In accordance with various embodiments described herein, the vaporized portion of the export stream 125 can be re-introduced into the distillation column 132 as the boil-up vapor stream 138. For example, once re-introduced into the distillation column 132, the boil-up vapor stream 138 can rise through the distillation column 132 and contact the liquid hydrocarbon feed stream 130 that is flowing down the distillation column 132.

At 222, the method 200 can comprise capturing the non-vaporized portion of the export stream 135 as a bottom product stream 140. In accordance with various embodiments described herein, the bottom product stream 140 can comprise NGL components that are heavier than the desired NGL product comprised within the product stream 124. Further, the bottom product stream 140 can be subject to further processing (e.g., cooling by one or more coolers 148) and supplied to one or more refinery operations. In one or more embodiments, the bottom product stream 140 can be supplied to one or more other processing modules 103 and be subject to one or more other implementations of method 200 to separate another NGL product.

For example, a first processing module 103 can execute a first implantation of method 200 using a deethanizer distillation column 132 and/or cooling unit 110 configuration to separate ethane as the product stream 124. Further, NGL processing system 100 can supply the bottom product stream 140 resulting from the first processing module 103 to a second processing module 103. For instance, the bottom product stream 140 can serve as the dry feed stream 108 for the second processing module 103. Additionally, the second processing module 103 can execute a second implementation of method 200 using a depropanizer distillation column 132 and/or cooling unit 110 configuration to separate propane as the product stream 124.

In another example, the NGL processing system 100 can supply the bottom product stream 140 resulting from the second processing module 103 to a third processing module 103. For instance, the bottom product stream 140 can serve as the dry feed stream 108 for the third processing module 103. Additionally, the third processing module 103 can execute a third implementation of method 200 using a debutanizer distillation column 132 and/or cooling unit 110 configuration to separate butane as the product stream 124.

It is to be further understood that like or similar numerals in the drawings represent like or similar elements through the several figures, and that not all components or steps described and illustrated with reference to the figures are required for all embodiments or arrangements.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "contains", "containing", "includes", "including," "comprises", and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized these terms could be used with reference to an operator or user. Accordingly, no limitations are implied or to be inferred. In addition, the use of ordinal numbers (e.g., first, second, third) is for distinction and not counting. For example, the use of "third" does not imply there is a corresponding "first" or "second." Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

The invention claimed is:
1. A method, comprising:
capturing overhead vapor from a distillation column;
comingling the overhead vapor with a non-cooled feed stream; and
partially condensing the non-cooled feed stream comingled with the overhead vapor to form a comingled liquid hydrocarbon feed stream from the non-cooled feed stream and the overhead vapor that is supplied to a top portion of the distillation column, wherein the comingling incorporates reflux functionality into the comingled liquid hydrocarbon feed stream to promote a rectification process in the top portion of the distillation column.

2. The method of claim 1, wherein the partially condensing the non-cooled feed stream comingled with the overhead vapor further comprises forming a comingled non-condensed vapor from the non-cooled feed stream and the overhead vapor, and the method further comprises supplying the comingled non-condensed vapor as a natural gas liquid product stream.

3. The method of claim 2, wherein the distillation column is a deethanizer, and wherein the natural gas liquid product stream is an ethane stream.

4. The method of claim 2, wherein the non-cooled feed stream has a higher temperature than the natural gas liquid product stream.

5. The method of claim 1, further comprising:
providing cooling from a propane refrigeration system to a chiller to cool the non-cooled feed stream comingled with the overhead vapor, thereby partially condensing the non-cooled feed stream comingled with the overhead vapor.

6. The method of claim 1, wherein the method excludes:
separately partially condensing either of the non-cooled feed stream or the overhead vapor to form a non-comingled liquid hydrocarbon feed stream from either of the non-cooled feed stream or the overhead vapor; and/or separately supplying the non-comingled liquid hydrocarbon feed stream from either of the non-cooled feed stream or the overhead vapor to the distillation column.

7. The method of claim 1, wherein the comingled liquid hydrocarbon feed stream comprises a first hydrocarbon component having the same boiling point as the overhead vapor and a second hydrocarbon component having a higher boiling point than the overhead vapor.

8. The method of claim 1, further comprising:
capturing a liquid bottom product stream from a bottom portion of the distillation column.

9. A system, comprising:
a piping circuit coupled to a top section of a distillation column, wherein the piping circuit is configured to capture overhead vapor from the distillation column;
a control valve positioned along the piping circuit, wherein the control valve is configured to control introduction of the overhead vapor to a non-cooled feed stream, thereby comingling the non-cooled feed stream and the overhead vapor; and
a cooling unit in fluid communication with the non-cooled feed stream comingled with the overhead vapor, wherein the cooling unit is configured to cool the non-cooled feed stream comingled with the overhead vapor, thereby partially condensing the non-cooled feed stream comingled with the overhead vapor to form a comingled liquid hydrocarbon feed stream from the non-cooled feed stream and the overhead vapor, wherein the piping circuit is further configured to supply the comingled liquid hydrocarbon feed stream to a top section of the distillation column, wherein the comingling incorporates reflux functionality into the comingled liquid hydrocarbon feed stream to promote a rectification process in the top portion of the distillation column.

10. The system of claim 9, wherein the system is not configured to: separately partially condense either of the non-cooled feed stream or the overhead vapor to form a non-comingled liquid hydrocarbon feed stream from either of the non-cooled feed stream or the overhead vapor; and/or separately supply the non-comingled liquid hydrocarbon feed stream from either of the non-cooled feed stream or the overhead vapor to the distillation column.

11. The method of claim 9, wherein the cooling unit is further configured to form a comingled non-condensed vapor from the non-cooled feed stream and the overhead vapor, and the piping circuit is further configured to supply the comingled non-condensed vapor as a natural gas liquid product stream.

12. The method of claim 11, wherein the distillation column is a deethanizer, and wherein the natural gas liquid product stream is an ethane stream.

13. The method of claim 11, wherein the non-cooled feed stream has a higher temperature than the natural gas liquid product stream.

14. The method of claim 9, wherein the cooling unit comprises a propane refrigeration system and a chiller, wherein the propane refrigeration system is configured to provide a cool propane stream to a chiller, and wherein the chiller is configured to cool the non-cooled feed stream comingled with the overhead vapor.

15. The method of claim 9, wherein the comingled liquid hydrocarbon feed stream comprises a first hydrocarbon component having the same boiling point as the overhead vapor and a second hydrocarbon component having a higher boiling point than the overhead vapor.

* * * * *